(12) United States Patent
Lacoste et al.

(10) Patent No.: US 8,221,338 B2
(45) Date of Patent: Jul. 17, 2012

(54) THERAPEUTIC TREATMENT APPLIANCE

(75) Inventors: Francois Lacoste, Paris (FR); Thierry Pechoux, Paris (FR)

(73) Assignee: Theraclion, Paris (FR)

( * ) Notice: Subject to any disclaimer, the term of this patent is extended or adjusted under 35 U.S.C. 154(b) by 432 days.

(21) Appl. No.: 12/518,722

(22) PCT Filed: Dec. 18, 2007

(86) PCT No.: PCT/FR2007/052545
§ 371 (c)(1),
(2), (4) Date: Jun. 15, 2009

(87) PCT Pub. No.: WO2008/081147
PCT Pub. Date: Jul. 10, 2008

(65) Prior Publication Data
US 2010/0016764 A1    Jan. 21, 2010

(30) Foreign Application Priority Data
Dec. 18, 2006   (FR) .................................... 06 55602

(51) Int. Cl.
*A61N 7/00*   (2006.01)
(52) U.S. Cl. .......................................................... 601/2
(58) Field of Classification Search ................. 601/2–4; 600/439; 604/22
See application file for complete search history.

(56) References Cited

U.S. PATENT DOCUMENTS

| 5,207,215 | A | * | 5/1993 | Rattner et al. | 601/4 |
| 5,601,526 | A | * | 2/1997 | Chapelon et al. | 601/3 |
| 5,759,162 | A | | 6/1998 | Oppelt et al. | |
| 6,818,012 | B2 | * | 11/2004 | Ellingboe | 607/104 |
| 2007/0260295 | A1 | * | 11/2007 | Chen et al. | 607/88 |

FOREIGN PATENT DOCUMENTS

| EP | 0614651 | 9/1994 |
| WO | 02/05897 | 1/2002 |

* cited by examiner

*Primary Examiner* — Ruth S Smith
(74) *Attorney, Agent, or Firm* — Shoemaker and Mattare

(57) ABSTRACT

A therapeutic treatment head for treating living tissue (T), the head comprising a casing (1), an ultrasound therapeutic transducer (2) mounted on the casing, and a diaphragm (3) mounted on the casing (1), the diaphragm (3) being designed to come into contact with an application surface (S) of the tissue (T), such as skin; the diaphragm (3), the transducer (2), and the casing (1) together defining a chamber (4) that is filled with an acoustic coupling liquid (L) that flows through the chamber between an inlet (41) and an outlet (42); the transducer (2) being placed in such a manner as to emit ultrasound through a propagation zone (Z) of the chamber towards the diaphragm (3); the head being characterized in that a first temperature sensor (51) is placed close to the inlet (41) and a second temperature sensor (52) is placed close to the outlet (42), the sensors (51, 52) delivering signals that are representative of temperatures.

9 Claims, 1 Drawing Sheet

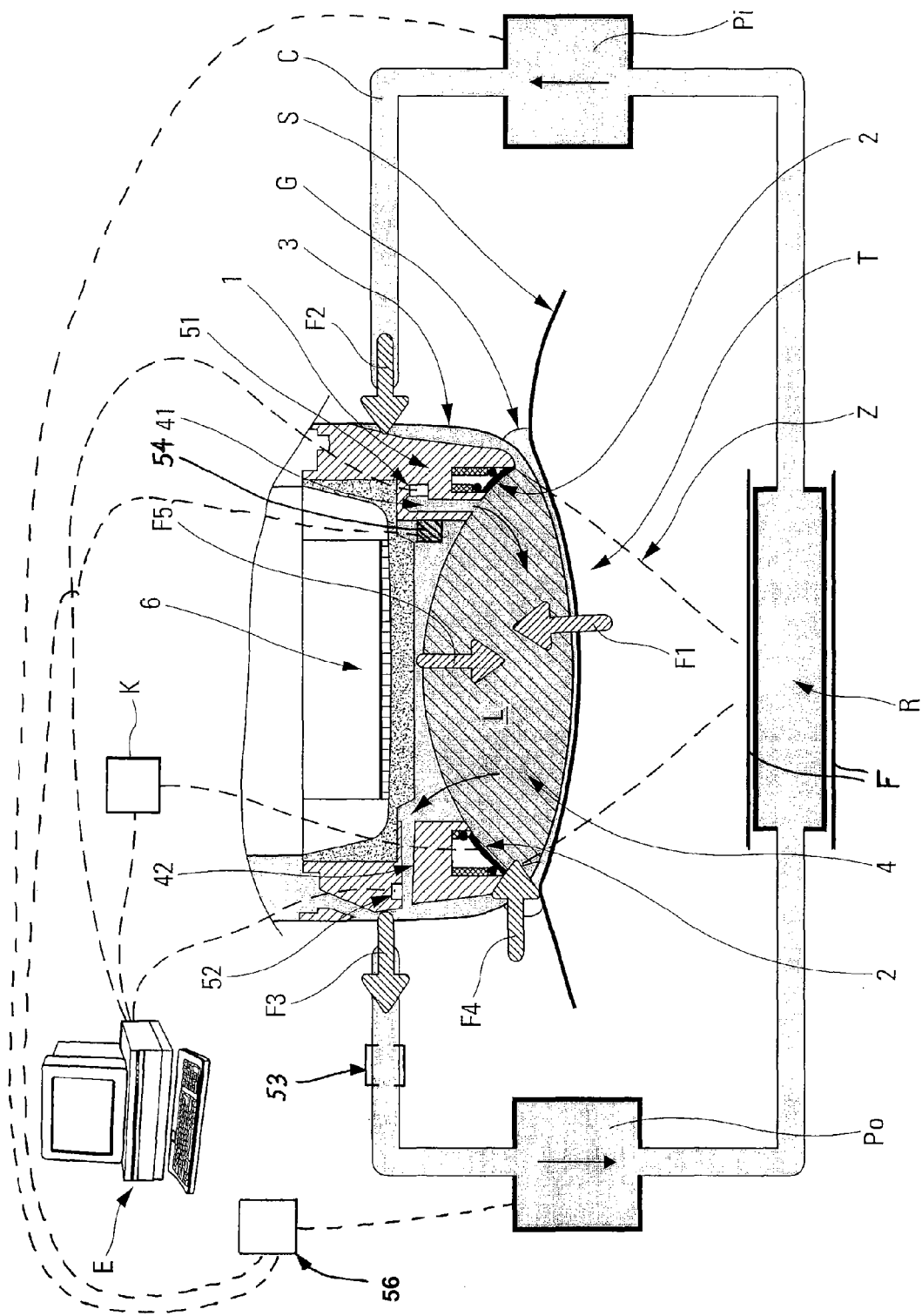

THERAPEUTIC TREATMENT APPLIANCE

The present invention relates to a therapeutic treatment head for treating living tissue. The present invention also relates to a therapeutic treatment appliance including such a therapeutic treatment head. In addition, the present invention also relates to a method of sequencing activation stages for the treatment head. Furthermore, the present invention relates to a method of indirectly determining the temperature of the application surface of the living tissue for treatment. Consequently, the preferred field of application for the present invention is that of therapeutic treatment appliances, instruments, and systems for treating living tissues. More particularly, the more restricted field of application is that of ultrasound therapeutic treatment.

Various types of ultrasound therapeutic treatment appliance are already known in the prior art that make use of therapeutic treatment heads implementing an ultrasound therapeutic transducer that emits ultrasound, e.g. a head of the high intensity focused ultrasound (HIFU) type. In general, the ultrasound therapeutic transducer is mounted on a casing of the head that forms a concave- or dome-shaped configuration. The ultrasound therapeutic transducer is mounted in the concave dome and thus also presents a concave dome-shape. In general, the treatment head also has a deformable flexible diaphragm mounted on the casing so as to form a chamber with the casing and the transducer. The chamber is conventionally filled with an acoustic coupling liquid, which may be water. The liquid flows through the chamber between an inlet and an outlet. To keep the liquid at a relatively low constant temperature, cooler means are often provided between the outlet and the inlet of the chamber. The transducer is located on the casing in such a manner as to emit ultrasound, preferably focused ultrasound, through a propagation zone of the chamber towards the diaphragm. In use, the diaphragm is designed to come into contact with an application surface of the tissue for treatment, such as the skin. The ultrasound emitted by the transducer thus passes through the propagation zone of the chamber, the diaphragm, the application surface of the tissue, and the tissue, and is in general focused on a target situated in the tissue. The ultrasound is thus absorbed by the tissue, with the amount of power absorbed being a function of the absorption capacity of the tissue and of the intensity of the ultrasound. This leads to a rise in the temperature of the tissue, which temperature rise depends on the absorbed power, on the heat capacity of the tissue, and also on heat losses, e.g. by conduction in the blood stream. Naturally, the acoustic coupling liquid flowing through the chamber serves to remove some of the heat, thus avoiding burning the tissue. Furthermore, the diaphragm makes it possible to facilitate acoustic contact when it is in intimate contact with the application surface of the tissue for treatment.

One of the problems associated with ultrasound treatment of tissue lies in monitoring the real absorption of the tissue, in particular at the interface between the head and the tissue, i.e. where the diaphragm touches the application surface of the tissue for treatment. When the treatment is extracorporeal, the application surface is the skin. If excessive heat is deposited on the skin, it will suffer thermal damage such as blistering or burning.

Another problem with ultrasound treatment of tissue lies in monitoring acoustic contact between the head and the tissue for treatment. It is possible that the diaphragm does not make good contact with the tissue, and this gives rise to ultrasound energy being reflected on the diaphragm, and as a result the treatment will be insufficient. In some circumstances, when the diaphragm makes no contact with the skin, there is even a risk of the transducer being destroyed. This can happen in particular when the diaphragm is spaced apart from the skin by a layer of air.

Another problem lies in controlling the amount of energy that is emitted by the transducer. It is possible that the head might break down, and for some reason the transducer might no longer emit enough ultrasound. The thermal treatment then no longer takes place in satisfactory manner.

Another problem consists in determining best sequencing for the application of ultrasound energy to the tissue. Prior to applying the diaphragm against the skin, the skin is at body temperature. It is necessary to wait a few minutes for the skin and the subcutaneous tissue to be cooled sufficiently to ensure that any heating created by the acoustic wave does not give rise to cutaneous or subcutaneous damage.

To summarize, the objects of the present invention are to avoid thermally damaging the application surface (skin) of the tissue for treatment, to detect poor contact between the head and the application surface of the tissue for treatment, and to detect poor operation of the transducer of the head.

To do this, the invention proposes a therapeutic treatment head for treating living tissue, the head comprising a casing, an ultrasound therapeutic transducer mounted on the casing, and a diaphragm mounted on the casing, the diaphragm being designed to come into contact with an application surface of the tissue, such as skin; the diaphragm, the transducer, and the casing together defining a chamber that is filled with an acoustic coupling liquid that flows through the chamber between an inlet and an outlet; the transducer being placed in such a manner as to emit ultrasound through a propagation zone of the chamber towards the diaphragm; the head being characterized in that a first temperature sensor is placed close to the inlet and a second temperature sensor is placed close to the outlet, the sensors delivering signals that are representative of temperatures. By way of example, these signals may be used to establish a treatment difference for the coupling liquid in the chamber, this difference serving indirectly to determine the temperature of the application surface. The temperature of the application surface (skin) of the tissue for treatment serves to determine whether there is a risk of burning, poor contact between the head and the application surface, or faulty operation of the transducer. The first solution that comes to mind is to measure the temperature of the application surface directly, e.g. by placing a temperature sensor on the diaphragm that is to come into contact with the application surface. Technically that might be possible, but the values measured with such a sensor mounted on the diaphragm would be erroneous because of the sensor being mounted in the zone through which the ultrasound emitted by the transducer propagates, thereby causing the sensor to absorb a portion of the ultrasound energy. The measured temperature values would therefore be erroneous, since they would be disturbed by interaction between the temperature sensor and the acoustic field. It is therefore not possible to measure the temperature of the application surface (skin) directly with the help of a temperature sensor mounted on the diaphragm. Furthermore, by placing the temperature sensor outside the ultrasound propagation zone, it is still not possible to measure the temperature of the application surface, even indirectly. That is why the present invention provides for two temperature sensors, advantageously disposed on either side of the chamber. Advantageously, the temperature sensors are situated outside the propagation zone. It is thus possible to measure a temperature difference continuously and to analyze the variations in the temperature difference in correlation with other factors or parameters so as to determine, deduce, or calculate, indirectly the temperature of the application surface (skin).

In general, the therapeutic treatment head of the invention is incorporated in a therapeutic treatment appliance that advantageously includes electronics receiving the temperature signals delivered by the temperature sensors in order to establish a temperature difference suitable for use in determining the temperature of the application surface. Advantageously, the electronics calculates the heat energy absorbed or rejected by the liquid in the chamber. Advantageously, the treatment appliance includes a liquid flow rate sensor delivering flow rate signals to the electronics in order to calculate the heat energy absorbed or rejected by the liquid in the chamber. Preferably, the treatment appliance includes cooler means for cooling the liquid prior to injecting it into the chamber through the inlet. Advantageously, the cooler means comprise at least one cooler plate exerting adjustable pressure on a reservoir pouch of liquid. The electronics thus receives the inlet and outlet temperature values delivered by the two sensors, and possibly also the values of liquid flow rate received by the flow rate sensor. Furthermore, the electronics may take account of ambient temperature and of heat losses from the ultrasound transducer. All ultrasound transducers present efficiency that is limited in the range about 50% to 80%. This means that 50% to 20% of the electrical energy delivered to the transducer is transformed into heat. By means of all of these measured values and these parameters, the electronics is capable of determining the temperature of the application surface of the tissue for treatment.

According to another characteristic of the invention, the appliance may include at least one pump and a pressure sensor coupled to a pressure regulator for regulating the pressure in the chamber.

In another advantageous aspect of the invention, the treatment appliance further includes switch means coupled to the electronics, the switch means deactivating the transducer when the temperature difference reaches a predetermined ceiling value indicative of the application surface overheating. Advantageously, the switch means activate the transducer when the temperature difference has come back below a predetermined threshold value indicative of a normal temperature for the application surface.

The invention also defines a method of sequencing activation stages for a transducer of a temperature head as defined above, wherein the transducer is activated and deactivated as a function of the temperature of the application surface as determined indirectly from the measured temperature difference. The temperature difference that is used for indirectly determining the temperature of the application surface (skin) thus serves as a trigger factor for activating and deactivating the ultrasound transducer. Thus, the operating cycle of the transducer is determined directly by the temperature difference or the temperature of the application surface is determined indirectly from the temperature difference. This avoids any risk of damaging the application surface and any risk of poor contact between the diaphragm and the application surface.

The present invention also defines a method of indirectly determining the temperature of the application surface in contact with a diaphragm of a therapeutic treatment head as defined above, characterized in that the temperature difference between the outlet and the inlet of the chamber is correlated with the flow rate of the liquid through the chamber in order to determine the temperature of the application surface. Advantageously, the temperature difference is correlated with ambient temperature in order to determine the temperature of the application surface. Advantageously, the temperature difference is correlated with the transducer energy that is dissipated as heat into the liquid of the chamber, in order to determine the temperature of the application surface.

The steps of indirectly determining the temperature of the application surface from the temperature difference, from the ambient temperature, and from the heat dissipated by the transducer are implemented by suitable software of the electronics. In an advantageous mode of operation, in an initial stage prior to activation of the transducer, the diaphragm is put into contact with the application surface until the estimated temperature of the application surface stabilizes sufficiently.

By determining the temperature of the application surface (skin) indirectly, it is thus possible to monitor the temperature of the skin so as to cool it sufficiently before beginning the therapeutic treatment (activation of the transducer) so as to avoid any risk of burning.

An advantageous principle of the invention is to determine the temperature of the application surface of living tissue for treatment indirectly by measuring a temperature difference of the acoustic coupling liquid within the chamber, and by correlating it with other external or internal parameters that act on the temperature of the coupling liquid. To summarize, the temperature difference becomes a value that is directly representative of the temperature of the application surface.

The invention is described in greater detail below with reference to the accompanying drawing showing an embodiment of the invention by way of non-limiting example.

The sole FIGURE is a diagrammatic fragmentary view of a therapeutic treatment appliance comprising a therapeutic treatment head of the invention, associated with electronics.

The therapeutic treatment appliance of the invention comprises a therapeutic treatment head that is shown in part only in the sole FIGURE. Only the bottom portion of the head that is of interest for the present invention is shown. The head also has a top portion (not shown) that serves for example to enable it to be mounted on a support structure and to be connected electrically or to an image data channel. The bottom portion of the head is shown diagrammatically in the sole FIGURE with an acoustic coupling liquid circuit. The head, and possibly also the circuit, is connected to processor electronics E, represented by a computer. The connections between the head and the electronics are drawn in dashed lines. The appliance also has a switch K that is connected both to the head and to the electronics E. The treatment head is shown here as being in contact with an application surface S of tissue T that is to be treated. In the description below, it is assumed that the application surface S is skin, even though it could be constituted by surfaces of other types, such as mucous membranes, or tissue having no skin or mucous membranes.

The therapeutic treatment head comprises a body or casing 1 that may be made of any other suitable material, such as metal, or advantageously of a material such as PEEK®. It is advantageous for the casing to be made of a material that is thermally insulating. The casing 1 serves as a support for numerous elements constituting the head, such as for example an ultrasound therapeutic transducer 2, a deformable flexible diaphragm 3, and an echographic probe 6. The casing 1 also defines an inlet channel 41 and an outlet channel 42. The casing 1 presents a bottom surface of concave configuration that is spherical or dome-shaped. The ultrasound therapeutic transducer 2 is fastened to this concave configuration so as to occupy the major portion thereof, even though that is not visible in the sole FIGURE. Thus, the transducer 2 also presents a dome-shaped configuration that is interrupted at a window in which the echographic probe 6 is positioned. The probe and the window are nevertheless optional. In general, the echographic probe 6 is an elongate probe, e.g. in the form of a strip, disposed in an elongate window that separates the therapeutic transducer 2 into two substantially symmetrical portions. The transducer 2 advantageously extends around the window in which the echographic probe 6 is positioned. The echographic probe 6 naturally has a function of providing an echographic display of the tissue for treatment. The function of the therapeutic probe 2 is to emit ultrasound, preferably focused ultrasound of the HIFU type towards a target inside the tissue T. It may also be observed in the sole FIGURE that the channels 41 and 42 open out in the concave configuration of the casing close to the window of the echographic probe 6.

The deformable flexible diaphragm 3 is fastened to the outside of the casing 1 by any appropriate means. The diaphragm extends in front of the concave configuration of the casing where the transducer 2 and the echographic probe 6 are mounted. The diaphragm 3, the casing, 1, the transducer 2, and the echographic probe 6 together define a chamber 4 of volume that is variable, given that the diaphragm 3 is deformable. The chamber 4 is filled with an acoustic coupling liquid L that may be water or a suitable gel. The liquid-filled chamber together with its diaphragm are commonly referred to as a "balloon". The chamber 4 communicates with the outside via the inlet channel 41 and the outlet channel 42. The channels 41 and 42 are connected to a circuit C that causes the acoustic coupling liquid L to be circulate through the chamber 4. At the outlet from the channel 42, the circuit may for example be provided with a flow rate sensor 53 that measures the flow rate of the coupling liquid in the circuit C. The flow rate sensor 53 delivers flow rate signals that are sent to the electronics E. The circuit C includes a liquid coupling reservoir pouch R. In order to cool it, this pouch is inserted in a bath of cold water between two cooled plates F, e.g. plates cooled by Peltier effect thermoelectric elements. The two plates F may be hinged together, thus enabling the pressure in the circuit to be adjusted by compressing the pouch R between the plates. Under such circumstances, a single plate F exerting pressure on the pouch R may suffice. The circuit C also includes at least one pump, and more particularly two pumps, an outlet pump $P_o$ and an inlet pump $P_i$. It is also possible to envisage using a single pump in the circuit C. Nevertheless, the use of two pumps makes it possible to guarantee a flow rate that is constant and at constant pressure. Advantageously, a pressure sensor 54 is located in the head, in communication with the coupling liquid and capable of measuring the pressure in the chamber. Information from the pressure sensor 54 and the pumps $P_i$ 9 and $P_o$ is sent to a pressure regulator 56. The two pumps can thus be controlled as a function of pressure information and optionally of fluid flow rate information. The pressure is regulated by applying a speed differential to the two pumps $P^i$ and $P_o$. The presence of two pumps thus also makes it easy to fill and empty the liquid in the chamber, by reversing their rotation. A bleed outlet may be provided in the top of the pouch R to facilitate removing liquid from the chamber and transferring it into the pouch. Thus, the liquid injected into the head via the inlet channel 41 is refrigerated and presents a temperature lower than the liquid in the outlet channel 42. Arrow F2 represents the heat flux injected by the flow of cooled liquid. Arrow F3 represents the heat flux extracted by the flow of liquid that has been heated in the chamber 4. Seen from the chamber 4, it can be considered that the inlet channel 41 constitutes the inlet to the chamber 4 while the outlet channel 42 constitutes the outlet from the chamber 4. Consequently, it should be understood throughout the description that the term "inlet channel" means inlet to the chamber 4, and the term "outlet channel" means outlet from the chamber 4.

With reference to the sole FIGURE, it can be seen that the diaphragm 3 is in contact with the skin S of tissue T, advantageously with a contact gel G being interposed between them. The diaphragm 3 is in contact with the skin S where the diaphragm forms the chamber 4. Thus, the skin at a temperature of about 30° C. transmits heat to the liquid L inside the chamber 4. Arrow F1 symbolizes the heat flow from the skin S to the liquid L.

Furthermore, the diaphragm 3 and the casing are also in contact with ambient air, which is generally at a temperature higher than the temperature of the liquid L. Consequently, air also delivers heat to the liquid L. Arrow F4 symbolizes the flow of heat from ambient air to the liquid L.

The ultrasound therapeutic transducer 2, and optionally the echographic probe 6, also dissipate heat inside the liquid L. Arrow F5 symbolizes the heat flow from the transducer 2, and possibly also from the probe 6, into the liquid L. It should be understood that all ultrasound transducers 2 dissipate a fraction of the energy supplied to them in the form of heat. The remainder is used for producing ultrasound. Given that the heat dissipated represents 20% to 50% of the energy supplied to the transducer, the quantity of heat that is dissipated inside the liquid L is considerable. In the sole FIGURE, the propagation zone Z for ultrasound from the transducer 2 into the chamber 4 is represented by shading. Outside the chamber, the propagation zone Z is represented by dashed lines. It can thus be observed that the major portion of the chamber 4 has ultrasound from the transducer 2 passing therethrough. In contrast, it can also be seen that the channels 41 and 42 and thus their temperature sensors 51 and 52 are not situated in the propagation zone Z for ultrasound from the transducer 2, nor in the echographic probe 6.

In the invention, a first temperature sensor 51 is placed close to or at the inlet of the chamber 4, and a second temperature sensor 52 is located close to or at the outlet from the chamber 4. More precisely, the sensor 51 is placed in the inlet channel 41 and the second sensor 52 is placed in the outlet channel 42. It is also possible to place the sensors 51 and 52 directly in the chamber 4 close to the inlet and the outlet, but preferably outside the wave propagation zone of the transducer 2 and of the probe 6. Thus, the first temperature sensor 51 serves to measure the temperature $T_i$ of the liquid entering the chamber 4, while the second temperature sensor 52 serves to measure the temperature $T_o$ of the liquid leaving the chamber 4. For example, by subtracting the temperature $T_o$ from the temperature $T_i$, a temperature difference $\Delta T$ is obtained for the coupling liquid in the channel. This temperature difference $\Delta T$ is used indirectly to determine the temperature of the skin.

This is done by means of the electronics E having connected thereto both temperature sensors 51 and 52 and also the flow rate sensor 53. The electronics E receives the temperature signals coming from the sensors 51 and 52 and flow rate signals coming from the sensor 53. The electronics E incorporates suitable software that serves to establish the temperature difference $\Delta T$ from the inlet and outlet temperatures $T_i$ and $T_o$ measured by the sensors 51 and 52. The electronics E also takes account of values for the flow rate, for the ambient temperature $T_a$, and for the heat dissipated by the transducer 2, and possibly also by the probe 6 inside the chamber 4. The electronics E can thus calculate the heat energy that is absorbed by or rejected by the liquid L in the chamber 4. The electronics E can calculate all of the heat flows F2 to F5, and on the basis thereof it can determine indirectly the heat flow F1, and finally the temperature of the skin.

An energy balance in terms of physics equations gives a clearer picture. Consideration should be given to all of the heat exchanges to which the coupling liquid is subjected in the chamber. Thus, these exchanges can be subdivided into four main heat flows, namely:

a) F3-F2: the difference between the incoming and outgoing liquid flows. The cold liquid entering the chamber delivers heat that is more than compensated by the heat in the heated liquid leaving the chamber.

b) The heat flow F1 through the diaphragm: since the temperature of the skin is higher than that of the liquid L, heat flows from the skin towards the liquid in the chamber.

c) The ambient air heat flow F4. The temperature of ambient air is higher than the temperature of the liquid, so heat is transferred from the ambient air to the liquid in the chamber.

d) The electro-acoustic flow F5: since the transducer is not perfectly efficient, the transducer heats up and delivers heat to the liquid in the chamber.

a) F3-F2: This corresponds to the power removed by the liquid. F3 represents the outgoing power while F2 represents the incoming power. In all, the power extracted can be calculated as follows:

$$\text{Power extracted } Pe = 4.1855(T_o D_o - T_i D_i)$$

where:
$T_i$=temperature of incoming water in ° C.;
$D_i$=mass flow rate of incoming water in grams per second (g/s);
$T_o$=temperature of outgoing heated water in ° C.; and
$D_o$=outgoing water mass flow rate in g/s. Under steady fluid flow conditions, $D_o = D_i$.

b) F1: since the temperature of the skin is higher than the temperature of the liquid, the heat flow from the skin to the liquid can be expressed as follows:

$$\text{Power\_supplied} = \frac{\lambda_m S}{E_m}(T_s - T_l)$$

where:
$T_s$=mean skin temperature in ° C. over the exchange structure S;
$T_l$=mean temperature of the liquid in the chamber, in ° C.;
S=exchange area of the diaphragm with the skin in square centimeters (cm²);
$E_m$=diaphragm thickness in centimeters (cm); and
$\lambda_m$=thermal conductivity of the diaphragm in watts per degree C. per centimeter (W/° C./cm).

It is possible to combine all of the constants into a single constant $k_m$ in W/° C.:

$$\text{Power\_supplied} = k_m(T_s - T_l)$$

where $$k_m = \frac{\lambda_m S}{E_m}$$

c) F4: Power supplied=$K_a(T_a - T_l)$
where:
$T_a$=mean temperature of ambient air in ° C. close to the treatment head;
$T_l$=mean temperature of the liquid in the chamber in ° C.; and
$K_a$=a constant associated with the shape and the materials used for the treatment head, in units of W/° C.

F5:

$$\text{Power\_supplied} = K_e P_e \left(\frac{tOn}{tOn + tOff}\right)$$

where:
tOn=duration of HIFU pulse emissions in seconds (s);
tOff=rest duration between HIFU pulses in s;
$P_e$=electrical power in watts (W) delivered to the transducer during pulses; and
$K_e$=a correction coefficient taking account of the acoustic efficiency of the transducer and of the effect of acoustic reverberation, and it has no units.

From these powers, it is possible to establish an equation for the heat balance under steady conditions. This is expressed as follows:

$$K_e P_e \left(\frac{tOn}{tOn + tOff}\right) + K_a(T_a - T_l) + k_m(T_s - T_l) = 4.1855(T_o D_o - T_i D_i)$$

It is thus possible to deduce the temperature of the skin as follows:

$$T_s = T_l + \frac{4.1855(T_o D_o - T_i D_i) - K_e P_e \left(\frac{tOn}{tOn + tOff}\right) - K_a(T_a - T_l)}{k_m}$$

It is also possible to establishes the heat balance equation under transient conditions. If the above equation for the heat balance is not in equilibrium, the temperature of the liquid in the head will be varying. It increases if the power supplied is greater than the power extracted, and vice versa.

$$\text{PowerDelivered} - \text{PowerExtracted} = 4.1855 \frac{dT_l}{dt} M_l$$

where:
$dT_l/dt$=the time derivative of the temperature of the liquid in the channel in ° C. per second (° C./s);
$M_l$=the mass of liquid in the chamber in grams (g);

$$K_e P_e \left(\frac{tOn}{tOn + tOff}\right) + K_a(T_a - T_l) + k_m(T_s - T_l) - 4.1855(T_o D_o - T_i D_i) =$$

$$4.1855 \frac{dT_l}{dt} M_l$$

It is thus possible to deduce the temperature of the skin from the following:

$$T_s = T_l + \frac{4.1855\frac{dT_l}{dt}M_l + 4.1855(T_oD_o - T_iD_i) - K_eP_e\left(\frac{tOn}{tOn+tOff}\right) - K_a(T_a - T_l)}{k_m}$$

Most of the data comprises constants that can be determined by setting parameters. The temperatures $T_i$ and $T_o$ are measured by the temperature sensors 51 and 52. The flow rate is measured by the sensor 53 or is known in advance. The ambient temperature can be measured by a thermometer. The mean temperature $T_m$ can be taken as the mean of $T_i$ and $T_o$. The flow F4 as a function of $T_m$ and $T_i$ or $T_l$ can be obtained by calibration.

The software in the electronics E performs calculations on the above temperature balance equations and determines the temperature of the skin of the tissue for treatment. In very general manner, the electronics E calculates the temperature difference ΔT and correlates it with the fluid flow rate, the external ambient temperature, and the heat dissipated by the transducer in the liquid in order to determine the temperature of the skin in indirect manner. Because of this measured temperature difference and the associated electronics E, it is possible to know whether the contact between the diaphragm 3 and the skin S is good, or on the contrary that the diaphragm has become locally or entirely separated from the skin. For example the diaphragm may be moved on the skin. If the contact area is large, and contact is therefore is of good quality, moving the diaphragm gives rise to only minimum variation in the temperature difference. In contrast, if the area is small, and contact is therefore of poor quality, moving the diaphragm will modify the contact zone and give rise to a considerable variation in the temperature difference. It is also possible to make use of the temperature difference to determine whether the transducer is, in fact, operating. If the transducer breaks down, either it is not receiving any electricity so no heat is dissipated into the liquid and the temperature difference will vary only little, or else it is receiving electricity but not emitting ultrasound, in which case the temperature difference will increase strongly. When the transducer is activated and is emitting ultrasound, estimating the temperature of the application surface enables the operator to be warned in the event of an excessive temperature rise of the skin. For this purpose, it is advantageous during an initial stage in which the transducer is not activated, to apply the diaphragm against the skin of the tissue for treatment and to cause the liquid to flow through the chamber until the temperature of the skin stabilizes so that the heat exchanged between the skin and the liquid in the chamber is close to a minimum. As soon as a stable skin temperature has been reached, treatment may begin quite safely for the skin. Similarly, it is possible to detect movements of the patient by monitoring the pressure in the chamber. For example, if the head moves away from the skin, the pressure will drop and the balloon will fill to compensate this pressure. By detecting variations in the volume of the balloon (via variations in the speeds of the pumps), it can be seen that coupling has been modified.

Given that the measured temperature differences are generally small, it is important for the measurements to be accurate. In order to eliminate differences, it is advantageous for example during a calibration stage to reverse the direction of liquid flow and thus perform two measurements, one in the forward direction and the other in the reverse direction. Furthermore, in order to minimize heat exchange, it is advantageous to make the casing out of a material that is known for its thermal insulation properties, such as for example PEEK®.

With reference once more to the sole FIGURE, it can be seen that the therapeutic treatment appliance may include a switch K that serves to activate and deactivate the therapeutic transducer 2. The switch K is shown coupled to the electronics E. According to an advantageous characteristic of the invention, the temperature difference ΔT, or the temperature $T_s$ of the skin as measured indirectly from the temperature differences ΔT, serves as a value for triggering the switch K. More precisely, the switch K deactivates the transducer 2 as soon as ΔT or $T_s$ reaches a predetermined ceiling value indicative of the skin over heating. Furthermore, the switch K will activate the transducer 2 as soon as ΔT or $T_s$ drops to a predetermined threshold value indicative of a normal or low temperature for the skin. In other words, sequences of activating the transducer of and resting the transducer are imposed by the switch K that is under the control of the electronics E, which makes use of the temperature difference or of the temperature of the skin in order to trigger the switch K. The operator in charge of the therapeutic treatment then no longer needs to worry about the temperature of the skin of the tissue for treatment, given that the transducer 2 is automatically activated and deactivated as a function of the temperature of the skin or of the temperature difference. This serves to reduce any risk of injuring the skin.

Estimating an abnormally low value for the temperature of the application surface (e.g. a temperature lower than the liquid temperature) corresponds to failure of a transducer, and more particularly to its lack of heat dissipation even though that is to be expected.

The switch K is automatically and directly triggered by the electronics E. In a variant, it is also possible to decouple the switch K from the electronics E. Under such circumstances, it is up to the operator performing the therapeutic treatment to activate and deactivate the transducer as soon as the temperature of the skin or the temperature difference reaches the ceiling value and the threshold value.

In a variant, it is possible momentarily to reduce the flow rate of the fluid circuit in order to increase ΔT and improve measurement accuracy.

By means of the invention, it is possible to use a temperature difference measured by two sensors in order to determine indirectly the temperature of the application surface of a tissue for treatment

The invention claimed is:

1. A therapeutic treatment appliance for treating living tissue (T), the appliance comprising
a casing (1),
an ultrasound therapeutic transducer (2) mounted in the casing, and
a diaphragm (3) mounted on the casing (1), the diaphragm (3) being designed to come into contact with an application surface (S) of the tissue (T);
the diaphragm (3), the transducer (2), and the casing (1) together defining a chamber (4) that is filled with an acoustic coupling liquid (L) that flows through the chamber between an inlet (41) and an outlet (42);
the transducer (2) being placed in such a manner as to emit ultrasound through a propagation zone (Z) of the chamber towards the diaphragm (3);
a first temperature sensor (51) placed close to the inlet (41) and a second temperature sensor (52) placed close to the outlet (42), the sensors (51, 52) delivering signals that are representative of temperatures, wherein the temperature sensors are situated outside the propagation zone; and electronics (E) receiving the temperature signals delivered by the temperature sensors (51, 52) to establish a temperature difference ($\Delta T$).

2. A therapeutic treatment appliance according to claim 1, wherein said temperature difference ($\Delta T$) is used for determining the temperature ($T_s$) of the application surface (S).

3. A therapeutic treatment appliance according to claim 2, wherein the electronics (E) calculates the heat energy absorbed or rejected by the liquid (L) in the chamber (4).

4. A therapeutic treatment appliance according to claim 2, including a liquid flow rate sensor (53) delivering flow rate signals to the electronics (E) in order to calculate the heat energy absorbed or rejected by the liquid (L) in the chamber (4).

5. A therapeutic treatment appliance according to claim 2, including cooler means (F) for cooling the liquid (L) prior to injecting it into the chamber (4) through the inlet (41).

6. A therapeutic treatment appliance according to claim 5, wherein the cooler means comprise at least one cooler plate (F) exerting adjustable pressure on a reservoir pouch (R) of liquid (L).

7. A therapeutic treatment appliance according to claim 2, including at least one pump ($P_i$, $P_o$) and a pressure sensor (54) coupled to a pressure regulator (56) for regulating the pressure in the chamber (4).

8. A therapeutic treatment appliance according to claim 2, including switch means (K) coupled to the electronics (E), the switch means deactivating the transducer (2) when the temperature difference ($\Delta T$) reaches a predetermined ceiling value indicative of the application surface (S) overheating.

9. A therapeutic treatment appliance according to claim 8, wherein the switch means (K) activates the transducer (2) when the temperature difference ($\Delta T$) has come back below a predetermined threshold value indicative of a normal temperature for the application surface (S).

* * * * *